(12) United States Patent
Mullen et al.

(10) Patent No.: US 10,316,009 B2
(45) Date of Patent: Jun. 11, 2019

(54) PROCESS TO PREPARE HYDROXYMETHYLFURFURAL DERIVATIVES

(71) Applicants: GFBIOCHEMICALS LIMITED, Valletta (MT); Brian D. Mullen, Delano, MN (US); Cora M. Leibig, Maple Grove, MN (US); Roger Schoonover, Beaverton, OR (US); Kevin Jon Bechtold, St. Paul, MN (US)

(72) Inventors: Brian D. Mullen, Delano, MN (US); Cora M. Leibig, Maple Grove, MN (US); Roger Schoonover, Beaverton, OR (US); Arie De Rijke, Brunssum (NL); Kevin Jon Bechtold, St. Paul, MN (US)

(73) Assignee: GFBIOCHEMICALS IP ASSETS B.V., Geleen (NL)

( * ) Notice: Subject to any disclaimer, the term of this patent is extended or adjusted under 35 U.S.C. 154(b) by 0 days.

(21) Appl. No.: 15/754,060

(22) PCT Filed: Aug. 19, 2016

(86) PCT No.: PCT/US2016/047790
§ 371 (c)(1),
(2) Date: Feb. 21, 2018

(87) PCT Pub. No.: WO2017/034985
PCT Pub. Date: Mar. 2, 2017

(65) Prior Publication Data
US 2018/0251439 A1 Sep. 6, 2018

Related U.S. Application Data

(60) Provisional application No. 62/208,208, filed on Aug. 21, 2015, provisional application No. 62/254,522, filed on Nov. 12, 2015.

(51) Int. Cl.
| | | |
|---|---|---|
| *C07D 307/50* | (2006.01) |
| *C07D 307/48* | (2006.01) |
| *C07D 307/54* | (2006.01) |
| *C07C 59/185* | (2006.01) |

(52) U.S. Cl.
CPC .......... *C07D 307/50* (2013.01); *C07C 59/185* (2013.01); *C07D 307/48* (2013.01); *C07D 307/54* (2013.01)

(58) Field of Classification Search
CPC .................................................... C07D 307/50
USPC ......................................................... 549/489
See application file for complete search history.

(56) References Cited

U.S. PATENT DOCUMENTS

| | | |
|---|---|---|
| 2010/0299991 A1 | 12/2010 | Gruter |
| 2012/0083610 A1 | 4/2012 | Gruter et al. |
| 2015/0210661 A1 | 7/2015 | Boussie et al. |

FOREIGN PATENT DOCUMENTS

| | | |
|---|---|---|
| WO | WO 2007/104515 | 9/2007 |
| WO | WO 2009/076627 | 6/2009 |
| WO | WO 2012/015616 | 2/2012 |
| WO | WO 2013/106136 | 7/2013 |

OTHER PUBLICATIONS

International Search Report and Written Opinion issued in International Application No. PCT/US2016/047790, dated Nov. 25, 2016.
Extended European Search Report issued in European Patent application No. 16839884.0, dated Jan. 4, 2019.

*Primary Examiner* — Taofiq A Solola
(74) *Attorney, Agent, or Firm* — Norton Rose Fulbright US LLP

(57) ABSTRACT

The invention relates generally to the preparation of hydroxymethyl furfural derivatives such as 5-carboxymethyl furfural derivatives, ethers such as 5-alkoxymethyl furfural derivatives, 5-hydroxymethyl furfural, levulinic acid, levulinic acid esters, and/or formic acid, formic acid esters from sugar.

20 Claims, No Drawings

PROCESS TO PREPARE HYDROXYMETHYLFURFURAL DERIVATIVES

CROSS-REFERENCE TO RELATED APPLICATIONS

This application is a national phase application under 35 U.S.C. § 371 of International Application No. PCT/US2016/047790 filed 19 Aug. 2016, which claims benefit of priority to U.S. Application No. 62/208,208 filed 21 Aug. 2015 and U.S. Application No. 62/254,522 filed 12 Nov. 2015, the entire contents of each is specifically incorporated by reference herein without disclaimer.

FIELD OF THE INVENTION

The invention relates generally to the preparation of hydroxymethyl furfural derivatives such as 5-carboxymethyl furfural derivatives, such as hydroxymethyl furfural acetate, hydroxymethyl furfural formate and hydroxymethyl furfural levulinate, ethers such as 5-alkoxymethyl furfural derivatives, such as 5-methoxymethyl-2-furfural and 5-hydroxymethyl furfural, levulinic acid, levulinic acid esters, formic acid, and/or formic acid esters from sugar.

BACKGROUND OF THE INVENTION

A major product in the acid-catalyzed dehydration of fructose is 2-hydroxymethyl-5-furfuraldehyde, also known as hydroxymethylfurfural (HMF).

HMF represents one key intermediate substance readily accessible from renewable resources like carbohydrates and is a suitable starting source for the formation of various furan monomers which are used for the preparation of non-petroleum-derived polymeric materials. HMF and its principle derivative, furandicarboxylic acid (FDCA) are molecules having an enormous potential, in particular for the production of polymers, in particular polyamides or polyesters, because of their structural similarities with terephthalic acid, a monomer usually used. While not being bound by theory, it is generally believed that fructose is converted to HMF via an acyclic pathway, although evidence also exists for the conversion to HMF via cyclic fructofuransyl intermediate pathways. Regardless of the mechanism of HMF formation, the intermediate species formed during the reaction may in turn undergo further reactions such as condensation, rehydration, reversion and other rearrangements, resulting in a plethora of unwanted side products. HMF can be obtained by dehydration, in an aqueous or solvent medium, of carbohydrates, in particular fructose, glucose or cellulosic material. However, the conversion and selectivity (and ultimately the yield) are low, in particular in purely aqueous or solvent media.

The lack of HMF selectivity of the carbohydrate dehydration reaction is explained by the rapidity of the secondary polymerization reactions of the reaction intermediates or of the HMF in a purely aqueous or solvent medium with an acid catalyst (for example, the formation of char).

Although preparation of HMF has been known for many years, a method which provides HMF with good selectivity and in high yields has yet to be found. Complications arise from the hydrolysis of HMF, which yields by-products, such as, levulinic and formic acids. Another unwanted side reaction includes the polymerization of HMF and/or fructose resulting in humin polymers, which are solid waste products. Further complications may arise as a result of solvent selection. Water is a relatively inexpensive solvent and dissolves fructose, but unfortunately, low selectivity and increased formation of polymers and humin increases under aqueous conditions.

Thus the selective production of HMF is complex, and its purification is difficult due to the instability of this molecule. It is also difficult to obtain HMF inexpensively. For these reasons, there is still no industrial-scale production of HMF.

Levulinic acid can be used to make resins, plasticizers, specialty chemicals, herbicides and as a flavor substance. Levulinic acid is useful as a solvent, and as a starting material in the preparation of a variety of industrial and pharmaceutical compounds such as diphenolic acid (useful as a component of protective and decorative finishes), calcium levulinate (a form of calcium for intravenous injection used for calcium replenishment and for treating hypocalcemia. The use of the sodium salt of levulinic acid as a replacement for ethylene glycols as an antifreeze has also been proposed.

Esters of levulinic acid are known to be useful as plasticizers and solvents, and have been suggested as fuel additives. Acid catalyzed dehydration of levulinic acid yields alpha-angelica lactone, which may be useful to make polymers.

Levulinic acid has been synthesized by a variety of chemical methods. But levulinic acid has not attained much commercial significance due in part to the high cost of the raw materials needed for synthesis. Another reason is the low yields of levulinic acid obtained from most synthetic methods. Yet, another reason is the formation of a formic acid byproduct during synthesis and its separation from the levulinic acid. Yet, still another reason is the formation of solid char by-products which are costly to remove from the process and need to be disposed, sold, or incinerated. Therefore, the production of levulinic acid has had high associated equipment costs. Despite the inherent problems in the production of levulinic acid, however, the reactive nature of levulinic acid makes it an ideal intermediate leading to the production of numerous useful derivatives.

BRIEF SUMMARY OF THE INVENTION

The invention relates generally to the preparation of hydroxymethyl furfural derivatives such as 5-carboxymethyl furfural derivatives, such as hydroxymethyl furfural acetate, hydroxymethyl furfural formate and hydroxymethyl furfural levulinate, ethers such as 5-alkoxymethyl furfural derivatives, such as 5-methoxymethyl-2-furfural and 5-hydroxymethyl furfural, levulinic acid, levulinic acid esters, formic acid, and/or formic acid esters from sugar.

In order to address the above mentioned problems, the disclosure provides a method of producing HMF derivatives, such as ethers or esters, and/or levulinic acid or levulinic acid derivatives, such as esters from a sugar source by contacting the sugar source with a catalyst (such as a solid phase catalyst), a reactive component, and optionally a co-solvent, which is preferably non-reactive.

In one embodiment, the disclosure provides a method of making an HMF derivative. The method includes the steps of providing sugar, providing a carboxylic acid, alcohol, or ketone, such as acetic acid, combining the sugar with the carboxylic acid, alcohol, or ketone to form a mixture, and heating the mixture in the presence of a catalyst in a reactor to a temperature of from about 40° C. to about 220° C. to provide a composition comprising the HMF derivative and between 0% and about 1% solid char.

In another embodiment, the disclosure provides a method for making an HMF derivative. The method includes the steps of providing sugar, providing a carboxylic acid, alcohol, or ketone, such as acetic acid, providing a co-solvent that is a hydrocarbon that does not contain a heteroatom, combining the sugar with the carboxylic acid, alcohol or ketone and the co-solvent to form a mixture, and heating the mixture in the presence of a catalyst in a reactor to a temperature of from about 40° C. to about 220° C. to provide a composition comprising the HMF derivative.

In another embodiment, the disclosure provides a method of producing HMF esters from a sugar source and carboxylic acids. In one embodiment, a sugar starting material is mixed with a carboxylic acid in the presence of a catalyst in a reactor to a temperature of from about 40° C. to about 220° C. to provide a composition comprising the HMF-ester and between 0% and about 1% solids.

In another embodiment, the disclosure provides a method for making an HMF ester. The method includes the steps of producing HMF esters from a sugar source and carboxylic acids. In one embodiment, a sugar starting material is mixed with a carboxylic acid to form a mixture having less than 5000 ppm of water and is heated in the presence of a catalyst in a reactor to a temperature of from about 40° C. to about 220° C. to provide a composition comprising the HMF-ester and between 0% and about 1% solids.

In another embodiment, the disclosure provides a method of producing HMF-acetate. The method includes the steps of adding acetic acid and high fructose corn syrup to a reactor to form a reaction mixture containing less than about 5000 ppm of water and between 0.01-20% sugar acetates, and heating the reaction mixture in the presence of a heterogeneous catalyst at a temperature from about 40° C. to about 220° C. to provide a composition comprising HMF-acetate.

In another embodiment, the disclosure provides a method of producing HMF-acetate including the steps of providing glacial acetic acid, providing high fructose corn syrup containing less than about 5000 ppm of water, providing a co-solvent containing less than about 5000 ppm of water, adding the glacial acetic acid, the high fructose corn syrup, and the co-solvent to a reactor to form a reaction mixture, and heating the reaction mixture in the presence of a heterogeneous catalyst at a temperature from about 40° C. to about 220° C. to provide a composition comprising HMF-acetate and optionally sugar acetates.

In another embodiment, the disclosure provides a method of producing 5-methoxymethyl-2-furfural, including the steps of providing methanol, providing high fructose corn syrup containing less than about 5000 ppm of water, providing a co-solvent containing less than about 5000 ppm of water, adding the methanol, the high fructose corn syrup, and the co-solvent to a reactor to form a reaction mixture, and heating the reaction mixture in the presence of a heterogeneous catalyst at a temperature from about 40° C. to about 220° C. to provide a composition comprising 5-methoxymethyl-2-furfural and optionally sugar ethers.

In another embodiment, the disclosure provides a method of producing 5-methoxy-2-furfural, including the steps of providing acetone, providing high fructose corn syrup containing less than about 5000 ppm of water, providing a co-solvent containing less than about 5000 ppm of water, adding the acetone, the high fructose corn syrup, and the co-solvent to a reactor to form a reaction mixture, and heating the reaction mixture in the presence of a heterogeneous catalyst at a temperature from about 40° C. to about 220° C. to provide a composition comprising 5-hydroxymethyl-2-furfural and optionally sugar acetonides.

In one embodiment, the resulting HMF derivative, such as an ester or ether, may be purified by filtration, evaporation, extraction, distillation or any combination thereof.

Advantages of the methods as described herein are the high rate of conversion of sugars into HMF, HMF ethers, HMF-esters and derivatives, such as levulinic acid, levulinic acid esters, formic acid esters, and/or formic acid. This results in a more stable form for HMF and a lower cost in materials.

Another advantage of the methods as described herein include the low amount of by-products formed from the subsequent oxidation of HMF-esters into furan dicarboxylic acid (FDCA). The HMF-esters under oxidation conditions would simply form FDCA and the carboxylic acid derived from the ester.

In another embodiment, there is provided a method for the synthesis of levulinic acid or levulinic ester by contacting a sugar with a carboxylic acid and optionally a co-solvent, to create a mixture having less than 5000 ppm of water and contacting the mixture with a solid phase catalyst under elevated temperature. HMF esters and/or levulinic acid and/or formic acid, which are more stable than HMF may be synthesized and purified by this process using a carboxylic acid, such as acetic acid.

A major issue in producing HMF and levulinic acid is the separation of pure levulinic acid and HMF from the byproducts, especially from formic acid and char. Current processes generally require high temperature reaction conditions, generally long digestion periods of biomass, specialized equipment to withstand hydrolysis conditions, and as a result, the yield of the levulinic acid is quite low, generally in yields of 10 percent or less.

Therefore, a need exists for a new approach that overcomes one or more of the current disadvantages noted above.

The present invention surprisingly provides novel approaches to more efficiently prepare HMF esters, which are important intermediates to levulinic acid and furan dicarboxylic acid, in commercial quantities with high yields and high purities.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, "LA" is intended to mean "levulinic acid."

As used herein, "HMF" is intended to mean "hydroxymethyl furfural" or "2-hydroxymethyl-5-furfuraldehyde."

As used herein, "HMF-Acetate" or "AMF" is intended to mean "5-acetoxy-methyl-furaldehyde."

As used herein, "HMF-ether" or "EMF" is intended to mean "5-alkoxy-methyl-furaldehyde."

As used herein, "FA" is intended to mean "formic acid."

As used herein, "sugar acetates" is intended to mean "acetate esters (mono- or multi-substituted) of fructose, glucose, or di-, and/or tri-saccharide combinations of glucose and fructose."

As used herein, "sugar ethers" is intended to mean "alkoxy ethers (mono- or multi-substituted) of fructose, glucose, or di-, and/or tri-saccharide combinations of glucose and fructose."

As used herein, "sugar acetonides" is intended to mean "acetonide ketals (mono- or multi-substituted) of fructose, glucose, or di-, and/or tri-saccharide combinations of glucose and fructose."

As used herein, "sugar ketals" is intended to mean "ketals (mono- or multi-substituted) of fructose, glucose, or di-, and/or tri-saccharide combinations of glucose and fructose."

As used herein, "char" or "solid char" is intended to mean organic insoluble byproducts from degradation reactions of sugar, HMF, AMF and/or LA.

As used herein, "FDCA" is intended to mean furan dicarboxylic acid.

The present invention provides various advantages in the preparation of hydroxymethyl furfural ester, such as HMF acetate, which can then be converted to levulinic acid, hydroxymethyl furfural, FDCA and/or formic acid. The following list of advantages is not meant to be limiting but highlights some of the discoveries contained herein.

First, a sugar material can be used as the initial feedstock to prepare the levulinic acid, hydroxymethyl furfural ester, such as HMF acetate and/or formic acid. This ability provides great flexibility in obtaining a constant source of starting material and is not limiting.

Second, the biomass can be a refined material, such as fructose, glucose, sucrose, mixtures of those materials and the like. As such, there is a plentiful supply of materials that can be converted into the ultimate product(s). For example, sugar beets or sugar cane can be used as one source. Fructose-corn syrup is another readily available material. Use of such materials thus helps to reduce the costs to prepare the desired products.

Third, it has been discovered that in some embodiments the essential absence of water from the reactants and the reaction provides a greater selectivity and yield for HMF ester, which is more stable than HMF.

Fourth, it has been discovered that in some embodiments the use of a carboxylic acid component and an optional non-reactive co-solvent leads to reaction product with less char and unwanted byproducts.

Fifth, it has also been found that the advantages of the new process conditions, including continuous addition of the sugar over a period of time during the reaction provides increased yields and selectivities to desired products.

Sixth, the processes described herein can be performed via batch, continuously fed batch, continuously stirred tank reactor, and plug flow conditions.

It has been found that other furan derivatives, particularly HMF esters and levulinic acid may be synthesized using the methods of the present invention. This method includes the steps of: i) combining materials comprising a sugar source, a carboxylic acid, an optional co-solvent and a catalyst, specifically a heterogeneous catalyst, to form a reaction mixture optionally having less than 5000 ppm, specifically less than 2500 ppm of water; ii) heating the reaction mixture to a temperature and for a time sufficient to promote an acid-catalyzed reaction of the sugar to form a product mixture that includes HMF ester, such as HMF acetate, levulinic acid, sugar acetate, formic acid, soluble tars and optionally from 0% to about 1% of solids; and iii) isolating an ester derivative, such as HMF acetate, and/or levulinic acid from the product mixture. HMF esters, such as HMF acetate, are more stable than HMF because they lack the exposed hydroxyl group of HMF.

It has been found that other furan derivatives, particularly HMF-ethers and levulinic acid may be synthesized using the methods of the present invention. This method includes the steps of: i) combining materials comprising a sugar source, an alcohol, an optional co-solvent and a catalyst, specifically a heterogeneous catalyst, to form a reaction mixture optionally having less than 5000 ppm, specifically less than 2500 ppm of water; ii) heating the reaction mixture to a temperature and for a time sufficient to promote an acid-catalyzed reaction of the sugar to form a product mixture that includes HMF-ether, such as EMF, and other optional components, including 0% to about 1% of solids, levulinic acid, sugar ethers, formic acid, levulinic acid ester, formic acid ester, and soluble tars, and optionally iii) isolating an ether derivative, such as EMF, and/or levulinic acid from the product mixture. HMF-ethers, such as EMF, are more stable than HMF because they lack the exposed hydroxyl group of HMF.

In one embodiment, the sugar is high fructose corn syrup, such as HFCS-90, HFCS-42, HFCS-55, sucrose, or inulin.

Suitable sugar sources typically include high fructose corn syrup (HFCS) or any HFCS refining process stream that includes at least 25% fructose. HFCS is typically commercially available in products comprising solutions having 42% to 95% fructose by solute weight which are typically sold for use as industrial scale sweeteners. In one embodiment of the invention HFCS having about 90% fructose by solute weight, such as HFCS 90 is utilized. However, other sources having less fructose by weight can also be used. In some embodiments, less pure fructose sources can be conveniently blended with higher purity fructose sources or even crystalline fructose to achieve a solution having at least 25% fructose by solute weight.

In some embodiments, prior to reaction, the sugar is provided in a form that contains less than 5000 ppm, more specifically less than 2500 ppm of water and even more specifically, less than 1000 ppm of water.

In one embodiment, the sugar is between about 0.1 to about 50%, more specifically, between about 0.2 to about 25%, more specifically, between about 1 to about 25%, and more specifically, between about 10 to about 20% by weight of the mixture of the sugar, the carboxylic acid, alcohol or ketone, the optional second catalyst and the optional co-solvent.

The reaction mixture also includes a carboxylic acid component, a ketone component, an alcohol component, or mixtures thereof. These components can function as solvents and/or reactants. Examples of carboxylic acids for use in the present invention include, but are not limited to, acetic acid, formic acid, propionic acid, lactic acid, oxalic acid, butyric acid, levulinic acid, pyruvic acid, trifluoroacetic acid, trichloroacetic acid, benzoic acid, and combinations thereof. Examples of alcohol components for use in the present invention include, but are not limited to, $C_1$-$C_{18}$ alcohols, including methanol, ethanol, propanol, butanol, pentanol, iso-butanol, hexanol, octanol, 2-ethylhexanol, iso-propanol, cyclohexanol, ethylene glycol, propane-diol, benzyl alcohol, trifluoroethanol, hexafluoroisopropanol, and mixtures thereof. Examples of reactive ketone components in the present invention include, but are not limited to, methyl ethyl ketone, acetone, methyl-isobutylketone, cyclohexanone, hexafluoro acetone, and methyl-isoamyl ketone.

In one embodiment, the carboxylic acid is acetic acid, specifically, glacial acetic acid having less than 5000 ppm of water and specifically less than 1000 ppm of water.

In one embodiment, the carboxylic acid, alcohol, or ketone component, such as acetic acid, is between about 0.1 to about 99.9% by weight of the mixture, specifically between about 1 to about 95% by weight of the mixture, more specifically between about 5 to about 90% by weight of the mixture, more specifically between about 10 to about 85% by weight of the mixture, more specifically between about 15 to about 75% by weight of the mixture, more specifically between about 20 to about 70% by weight of the mixture, and more specifically between about 30 to about 60% by weight of the mixture of the sugar, the carboxylic acid, alcohol or ketone, the optional second catalyst and the optional co-solvent.

In some embodiments the reaction mixture comprises a co-solvent. The co-solvent can be reactive or non-reactive. In one embodiment, the co-solvent is a hydrocarbon that does not contain a heteroatom, such as cyclohexane, toluene, mineral oil, cyclopentane, pentane, hexane, heptane, octane, kerosene, benzene, xylenes, alkyl substituted cyclohexanes, alkyl-substituted or branched alkanes or aromatics. In other cases, the co-solvent contains a heteroatom, such as, DMSO, DMAC, DMF, NMP, ethyl acetate, butyl acetate, iso-propyl acetate, propyl acetate, glycol ethers, MTBE, d-limonene, acetic anhydride, tetrahydrofuran (THF), methyl-THF, gamma-valerolactone, diethyl ether, acetone, cyclohexanone, methyl ethyl ketone, methyl isobutyl ketone (MIBK), ionic liquids, chlorinated solvents, like methylene chloride, dichloro-ethane, chloro-benzene, or ortho-dichloro benzene. In one embodiment, the co-solvent is cyclohexane. In another embodiment, the co-solvent is toluene. In another embodiment, the co-solvent is DMSO.

In one embodiment, the co-solvent has less than 5000 ppm of water, specifically less than 2500 ppm of water, and more specifically less than 1000 ppm of water.

In one embodiment, the co-solvent is between about 0.1 to about 95%, more specifically between about 1 to about 90%, more specifically between about 1 to about 90%, more specifically between about 2 to about 80%, more specifically between about 10 to about 70%, and more specifically between about 40 to about 60% by weight of the mixture of the sugar, the carboxylic acid, ketone or alcohol, the optional second catalyst and the co-solvent.

Without wishing to be bound by theory, it is believed that the co-solvent lowers the energetics of the reaction of sugar dehydrating to form HMF and/or HMF-ester, and/or HMF-ether, and thus provides a selectivity enhancement and a conversion enhancement toward desired product. For example, the use of a co-solvent with acetic acid results in higher conversion to the desired product, HMF and/or HMF-acetate and lower conversion to soluble tars and insoluble char byproducts. This is an unexpected advantage and provides a surprisingly, high sugar utilization with minimal byproducts when the process is conducted in the presence of a co-solvent. Also, it is surprising that the hydrolysis reaction of HMF and/or HMF-acetate to LA is selective as well. In nearly every reference in the prior art for the last 100 years in which LA is formed from HMF and/or sugar, there are soluble tars and insoluble char that forms. Many embodiments of the process of this invention, such as the co-solvent system with acetic acid, prevent or minimize insoluble char and soluble tar formation.

Reusable or recyclable heterogeneous catalysts are preferred for use in the reaction, as they provide for increased efficiency, and economic and industrial feasibility. As used herein, the term "recyclable catalyst" refers to a catalyst which is not irreversibly expended as a result of a single reaction. In other words, the catalyst may be used again. Examples of recyclable or reusable catalysts include, but are not limited to, solid acid catalysts, ion-exchange resins, zeolites, Lewis acids, clays, and molecular sieves. Solid acid catalysts often comprise a solid material which has been functionalize to impart acid groups that are catalytically active. Solid acid catalysts may have a broad range of composition, porosity, density, type of acid groups and distribution of acid groups. Solid acid catalysts may be recovered and reused, optionally with a treatment to regenerate any activity that may have been lost in use. Some solid acid catalysts that may be used in the disclosed process include, but are not limited to Amberlyst 35, Amberlyst 45, Amberlyst 15, Amberlyst 131, Amberlyst 70, Amberlyst BD-20 (Dow Chemical), Lewatit S2328, Lewatit K2431, Lewatit S2568, Lewatit K2629 (Sybron Corp, Birmingham, N.J.), Dianion SK104, Dianion PK228, Dianion RCP160, RCP21H, Relite RAD/F (Mitsubishi Chemical, White Plains, N.Y.), and Dowex 50WX4, Dowex 50WX8 (Dow Chemical), Nafion®-type catalysts, such as Nafion® NR-50 and Nafion® SAC-13, or other fluorinated polymers containing —$CF_x$—$SO_3H$ (x=1 or 2) substituents pendant to the fluoro-polymer backbone. Also, inorganic catalysts such as sulfated zirconia, heteropolyphosphates, heteropolytungstates, sulfated silica, zirconium phosphate, or sulfated zeolites may be used.

In some embodiments, the catalyst used in the method of the present invention is a solid or heterogeneous, catalyst. In one embodiment the catalyst is a sulfonic acid ion exchange resin, such as Amberlyst 15, Amberlyst 35, Amberlyst 70, or any combination thereof. In other embodiments, the catalyst is a homogeneous catalyst, such as a mineral acid, such as, but not limited, to sulfuric acid, hydrochloric acid, hydrobromic acid, hydroiodic acid, nitric acid, phosphoric acid, boric acid, hydrofluoric acid, perchloric acid, p-toluene sulfonic acid, methane sulfonic acid, benzene sulfonic acid, ethane sulfonic acid, camphor sulfonic acid, and mixtures thereof.

In one embodiment, the catalyst is a first catalyst, and a second catalyst is also used in the reaction. In some embodiments, the second catalyst is a homogeneous catalyst, such as a mineral acid, such as, but not limited, to sulfuric acid, hydrochloric acid, hydrobromic acid, hydroiodic acid, nitric acid, phosphoric acid, boric acid, hydrofluoric acid, perchloric acid, p-toluene sulfonic acid, methane sulfonic acid, benzene sulfonic acid, ethane sulfonic acid, camphor sulfonic acid, and mixtures thereof.

In some embodiments, the homogeneous catalyst is less than 5%, more specifically, less than 3% by weight of the mixture of sugar, carboxylic acid, alcohol or ketone, optional co-solvent and the homogeneous catalyst.

The methods of the present invention can be carried out in a variety of different reactors. In one embodiment, the reactor is a batch reactor. In another embodiment, the reactor is a continuously fed batch reactor. In another embodiment the reactor is a continuously stirred tank reactor (CSTR). In another embodiment, the reactor is a plug flow reactor (PFR). In some embodiments, the reactor is part of a reactor system. In one embodiment, the reactor system includes a plurality of CSTRs. In another embodiment, the reactor system includes a plurality of PFRs. In yet another embodiment, the reactor system includes a combination of one or more CSTRs and one or more PFRs.

In one embodiment, to conduct a CSTR reaction with a given "residence time" t (in this case, t=typically 10 min to 3 hours) the volume of the reactor is selected such that the typical "residence time" of the reactants is the designed target. The mass of material held in the reactor is designed to be the product of the mass flow rate into the reactor and the residence time. Longer residence time=larger quantity of material held in the reactor. Slower feed rate=smaller quantity of material held in the reactor. In operation, it is desirable for the feed to be a constant flow rate and composition; also the exit stream is a constant flow rate and composition, and the sum of the flow rates of all exit streams equals the flow rate of the feeds (on a mass basis).

Typically, the reactor goes through a start-up phase until the reactor achieves "steady state" wherein the reactor contents, temperature, and pressure only varies within a controlled range. After steady state is achieved, the reactor is continuously operated as long as desired (days, weeks, months, years). During operation, the feed is steady, and the exit stream is steady. The reactor contents are steady. But the average residence time of the reactor contents is designed and held constant. The reactor content composition is equal to the composition of the exit streams.

During the startup phase, many strategies can be used to reach steady state as quickly as possible. For example, the reactor contents may be fed with the desired steady state composition of the reactor contents. The composition of the feed streams can be allowed to vary, and the flow rate of the exit stream may be varied to achieve steady state (anywhere from zero to equal to the feed rate).

It has been observed that the production of HMF could potentially lead to large amounts of undesirable char build up. For example, a CSTR design which is inadvertently designed so as to run at conditions which give a high HMF yield at a high temperature, could be expected to yield high char and discouraging results.

It is thus, one technical advantage of one embodiment of the invention to provide a continuous reaction system in such a way to minimize the HMF concentration at high temperatures (Temperatures above 130° C.).

In one embodiment, the reactions disclosed herein are performed at moderately high temperatures, typically in a range of from about 40° to about 220° C. In a further embodiment, the temperature range is from about 60° C. to about 130° C., more specifically from about 60° C. to about 100° C. In one embodiment, the temperature is below 120° C., more specifically 110° C. and more specifically 100° C. The reactions disclosed herein typically occur in a time frame of from about 5 minutes to about sixteen hours, more specifically, the reactions take from about 10 minutes to about twelve hours, more specifically from about 40 minutes to about four hours, and more specifically from about 1 hour to about 3 hours. If additional steps regarding the isolation and purification of HMF esters such as AMF or other materials such as LA, HMF or FA are preformed, additional time may be required. In one embodiment, HMF ester, specifically HMF acetate, or HMF-ether, is isolated and recovered. In another embodiment, levulinic acid or levulinic acid ester is isolated and recovered. In another embodiment, formic acid is isolated and recovered. In another embodiment, HMF is isolated and recovered.

In one embodiment, the carboxylic acid, alcohol or ketone component, the optional non-reactive co-solvent, the optional homogeneous catalyst and the sugar are combined prior to introduction into a reactor. In one embodiment, the mixture is formed and heated then introduced into the reactor. In another embodiment, the sugar is combined with some carboxylic acid, alcohol or ketone component and the resulting mixture, optionally heated to remove water, is then introduced into a reactor containing the catalyst and more of the carboxylic acid, alcohol or ketone component.

In one embodiment, the sugar is added to the reactor, either separately from or mixed with the carboxylic acid, alcohol or ketone, at a rate such that the sugar content of the mixture remains less than or equal to about 5% by weight of the reaction mixture during the entire reaction.

The resulting compositions from the reaction may contain HMF, HMF esters, such as HMF acetate, HMF-ethers, sugar esters, such as sugar acetate, sugar ethers, sugar acetonides, sugar ketals, levulinic acid, levulinic acid esters, formic acid, formic acid esters, and/or soluble tars. In some embodiments, the product compositions will contain between 0% and about 1% solids. It has been found that in some embodiments, by keeping the water levels low in the reactants (less than 5000 ppm, specifically less than 1000 ppm) and optionally removing water that is formed during the reaction from the reactor, that the reaction is more selective to HMF-esters or HMF-ethers, and less selective to HMF, which is reactive and tends to react to form unwanted humin solids, or char. The creation of char creates operability issues for the production of HMF and levulinic acid by plugging reactors and creating the need for solids handling.

In certain embodiments of the method, over 40%, more specifically, over 50%, more specifically, over 60%, and more specifically over 70% of sugars present in the starting reactants are converted to HMF ester or HMF-ether, the percent conversion being calculated by molar yield. Yield may be increased by altering any of the variables, such as solvent type, concentration, catalyst, time and/or temperature of the reaction conditions, etc. It has been further found that in some embodiments, the removal of water from the reaction components prior to reaction increases the yield of HMF-ester or HMF-ether. In one embodiment, the sugar does not exceed 75% conversion during the reaction. It has been observed that once sugar conversion exceeds 75%, unwanted by products begin to form at higher rates. By removing water prior to reaction, and optionally pulling water that is formed by the reaction out of the reactor during the reaction, side-reactions are thereby minimized, and increased selectivity has been observed. A distillation column or an evaporator with or without the use of an entrainer may be employed to promote water removal. The use of a distillation column, an evaporator, or an entrainer to remove water is known in the art. Water may also be removed by azeotropic distillation with a water-entraining solvent which may optionally be stripped of water and the water depleted solvent returned to the reaction vessel. A water-absorbing material may also be used to remove water. Such materials are well-known in the art, and include, but are not limited to, molecular sieves. The water may be removed optionally during the reaction.

It has also been observed that in some embodiments, by removing water from the reaction components, controlling the addition rates of the reaction components and optionally further removing water from the reactor during the reaction, the reaction is greater than 50%, greater than 60%, greater than 70% and even greater than 80% selective to forming HMF-ester, specifically HMF-acetate.

In one embodiment, the method of the present invention also produces sugar esters, such as sugar acetates, sugar ethers, sugar acetonides, or sugar ketals. In one embodiment, the sugar esters are hydrolyzed with water and the sugar and acetic acid is recycled back to a reactor feed inlet for further reaction. In another embodiment, the sugar ethers are hydrolyzed with water and the sugar and alcohol are recycled back to a reactor feed inlet for further reaction. In one embodiment, the sugar acetonides are hydrolyzed with water and the sugar and acetone are recycled back to a reactor feed inlet for further reaction. In one embodiment, the sugar ketals are hydrolyzed with water and the sugar and ketone are recycled back to a reactor feed inlet for further reaction. Optionally, the glucose that is produced from the hydrolysis of sugar acetates, sugar ethers, sugar acetonides, or sugar ketals is cleaned to remove impurities and isomerized into fructose before it is recycled back to the reactor feed inlet for further reaction. Optionally, the carboxylic acid, alcohol or ketone is extracted with an extraction solvent, such as cyclohexane, and is recycled back to the reactor after removing the extraction solvent. Optionally, the soluble tars are precipitated and removed from the sugar acetate stream prior to hydrolysis of the sugar acetate and recycle of the sugar back into the reactor feed inlet. Optionally, the soluble tars are removed by extraction with an extraction solvent that also extracts acetic acid. Optional neutralization of the product isolate is carried out by addition of a suitable alkali substance, such as a basic ion exchange resin, lime, slaked lime, potassium hydroxide, or sodium hydroxide. This neutralization step allows for subsequent product recovery by distillation without heat-catalyzed degradation or polymerization, resulting in the elimination of tarry degradation products and resinous solids being formed in distillation.

In one embodiment, the HMF-derivative, such as the ester or ether, is further reacted to form LA, FA and/or FDCA. In one embodiment the HMF-ester, HMF-ether, and/or HMF that is formed is recycled back into the reactor to form additional LA or LA ester.

In one embodiment, LA formed during the reaction is recycled back to the reactor. In another embodiment, LA formed after further converting the HMF derivative is recycled back to the reactor. In another embodiment, the LA formed during the reaction is isolated by distillation, crystallization, precipitation, neutralization, extraction, or a combination of 1 or more methods.

In another embodiment, LA formed by the process of the present invention is optionally isolated and is converted to other commercially useful products, such as succinic acid, suberic acid, gamma valero lactone, angelica lactone, methylene valero lactone, alkyl levulinates, such as ethyl levulinate and methyl levulinate, levulinic ketals, such as those formed from the reaction of ethyl levulinate and propylene glycol or glycerol, diphenolic acid as well as others.

The following paragraphs provide for various aspects of the present invention. In one embodiment, in a first paragraph (1), the present invention provides a method for making an HMF-ester and levulinic acid, the method comprising the steps of:

mixing sugar with a carboxylic acid to form a mixture having less than 5000 ppm of water; and heating the mixture in the presence of a catalyst in a reactor to a temperature of from about 40° C. to about 220° C. to provide a composition comprising the HMF-ester and between 0% and about 1% solid char.

2. The method of paragraph 1, wherein the sugar is high fructose corn syrup, sucrose or inulin.

3. The method of paragraph 2, wherein the high fructose corn syrup is HFCS-90.

4. The method of any of paragraphs 1 through 3, wherein the mixture contains less 2500 ppm of water.

5. The method of any of paragraphs 1 through 4, wherein the catalyst is a heterogeneous catalyst.

6. The method of paragraph 5, wherein the catalyst is a sulfonic acid ion exchange resin.

7. The method of paragraph 6, wherein the catalyst is Amberlyst 15, Amberlyst 35, Amberlyst 70, Amberlyst BD20, or any combination thereof.

8. The method of any of paragraphs 1 through 7, wherein the catalyst is a first catalyst, further comprising a second catalyst in the mixture.

9. The method of paragraph 8, wherein the second catalyst is a homogeneous catalyst.

10. The method of paragraph 9, wherein the second catalyst is sulfuric acid.

11. The method of paragraph 10, wherein the sulfuric acid is less than about 5% by weight of the mixture.

12. The method of any of paragraphs 1 through 11, wherein the sugar and carboxylic acid are mixed together prior to introduction into the reactor.

13. The method of paragraph 12, wherein the sugar and carboxylic acid are heated to remove water prior to introduction into the reactor.

14. The method of any of paragraphs 1 through 13, the mixture further comprising a co-solvent.

15. The method of paragraph 14, wherein the co-solvent is a hydrocarbon that does not contain a heteroatom.

16. The method of paragraph 14, wherein the co-solvent is a hydrocarbon that contain a heteroatom.

17. The method of paragraph 15, wherein the co-solvent is cyclohexane.

18. The method of paragraph 15, wherein the co-solvent is DMSO.

19. The method of paragraph 15, wherein the co-solvent is THF.

20. The method of any of paragraphs 14 through 19, wherein the co-solvent is between about 0.1 to about 95% by weight of the mixture.

21. The method of paragraph 20, wherein the co-solvent is between about 1 to about 90% by weight of the mixture.

22. The method of paragraph 20, wherein the co-solvent is between about 40 to about 80% by weight of the mixture.

23. The method of any of paragraphs 1 through 22, wherein the sugar is between about 0.1 to about 50% by weight of the mixture.

24. The method of paragraph 23, wherein the sugar is between about 0.2 to about 25% by weight of the mixture.

25. The method of paragraph 23, wherein the sugar is between about 5 to about 20% by weight of the mixture.

26. The method of any of paragraphs 1 through 25, wherein the carboxylic acid is acetic acid.

27. The method of any of paragraph 1 through 26, wherein the carboxylic acid is between about 0.1 to about 99.9% by weight of the mixture.

28. The method of paragraph 27, wherein the carboxylic acid is between about 1 to about 95% by weight of the mixture.

29. The method of paragraph 27, wherein the carboxylic acid is between about 5 to about 90% by weight of the mixture.

30. The method of paragraph 27, wherein the carboxylic acid is between about 10 to about 85% by weight of the mixture.

31. The method of any of paragraphs 1 through 30, wherein the carboxylic acid and sugar each contain less than about 5000 ppm of water prior to mixing.

32. The method of paragraph 31 wherein the carboxylic acid and sugar each contain less than about 1000 ppm of water prior to mixing.

33. The method of any of paragraphs 1 through 32, wherein the mixture is heated in the presence of a catalyst to a temperature of from about 60° C. to about 130° C.

34. The method of any of paragraphs 1 through 32, wherein the mixture is heated in the presence of a catalyst to a temperature of from about 60° C. to about 100° C.

35. The method of any of paragraphs 1 through 34, wherein the composition comprises HMF.

36. The method of any of paragraphs 1 through 35, wherein the composition comprises sugar acetate.

37. The method of any of paragraphs 1 through 36, wherein the composition comprises soluble tars.

38. The method of any of paragraphs 1 through 37, wherein the composition comprises formic acid.

39. The method of any of paragraphs 1 through 38, wherein the composition comprises levulinic acid.

40. The method of any of paragraphs 1 through 39, wherein the reactor is a batch reactor.

41. The method of any of paragraphs 1 through 39, wherein the reactor is a continuous addition batch reactor.

42. The method of any of paragraphs 1 through 39, wherein the reactor is a continuous stirred tank reactor.

43. The method of paragraph 42, wherein the reactor is a reactor system having a series of 2 or more continuous stirred tank reactors.

44. The method of paragraph 43, wherein the total amount of sugar is introduced in fractional amounts in each continuous stirred tank reactor.

45. The method of any of paragraphs 1 through 39 wherein the reactor is a plug flow reactor.

46. The method of paragraph 45, wherein the reactor is a reactor system having a series of 2 or more plug flow reactors.

47. The method of paragraph 46, wherein the total amount of sugar is introduced in fractional amounts in each plug flow reactor.

48. The method of any of paragraphs 42 through 47, wherein the reactor system is a combination of CSTRs and plug flow reactors.

The method of any of paragraphs 1 through 47, wherein the mixture has a residence time in the reactor between about 5 minutes and about 12 hours.

49. The method of any of paragraphs 1 through 47, wherein the mixture has a residence time in the reactor between about 5 minutes and about 12 hours, more specifically between about 10 minutes minute and about 16 hours.

50. The method of any of paragraphs 1 through 47, wherein the mixture has a residence time in the reactor between about 20 minutes and about 4 hours.

51. The method of any of paragraphs 1 through 50, wherein the sugar is added to the reactor at a rate such that the sugar content of the mixture remains less than or equal to about 5% by weight of the mixture during the entire reaction.

52. The method of any of paragraphs 1 through 51, wherein the reaction is greater than 50% selective to forming a combination of HMF-acetate, HMF, and LA versus non-selective by-products (tar and char).

53. The method of any of paragraphs 1 through 51, wherein the reaction is greater than 60% selective to forming a combination of HMF-acetate, HMF, and LA versus non-selective by-products (tar and char).

54. The method of any of paragraphs 1 through 51, wherein the reaction is greater than 70% selective to forming a combination of HMF-acetate, HMF, and LA versus non-selective by-products (tar and char).

55. The method of any of paragraphs 1 through 51, wherein the reaction is greater than 80% selective to forming a combination of HMF-acetate, HMF, and LA versus non-selective by-products (tar and char).

56. The method of any of paragraphs 1 through 55, wherein the sugar and sugar acetate conversion does not exceed 75% conversion during the reaction.

57. The method of any of paragraphs 1 through 55, wherein the sugar and sugar acetate conversion does not exceed 90% conversion during the reaction.

58. A method for making HMF-acetate, the method comprising the steps of
adding acetic acid and high fructose corn syrup to a reactor to form a reaction mixture containing less than about 5000 ppm of water and between 0.01-20% sugar acetates; and
heating the reaction mixture in the presence of a heterogeneous catalyst at a temperature from about 40° C. to about 220° C. to provide a composition comprising HMF-acetate.

59. A method for making HMF-acetate, the method comprising the steps of
providing glacial acetic acid;
providing high fructose corn syrup containing less than about 5000 ppm of water;
providing cyclohexane containing less than about 5000 ppm of water;
adding the acetic acid, the high fructose corn syrup, and the cyclohexane to a reactor to form a reaction mixture; and
heating the reaction mixture in the presence of a heterogeneous catalyst at a temperature from about 40° C. to about 220° C. to provide a composition comprising HMF-acetate.

60. The method of any of paragraphs 1 through 59, wherein the composition comprises sugar acetates and wherein the sugar acetates are recycled back to a reactor feed inlet by a hydrolysis step.

61. The method of any of paragraphs 1 through 60, further comprising isolating and recovering HMF-acetate.

62. The method of any of paragraphs 1 through 61, further comprising isolating and recovering HMF.

63. The method of any of paragraphs 1 through 62, further comprising isolating and recovering LA.

64. The method of any of paragraphs 1 through 63, further comprising isolating and recovering formic acid.

65. The method of any of paragraphs 1 through 64, wherein the sugar comprises glucose, further comprising the step of isomerizing the glucose into fructose before it is recycled back into the reaction inlet.

66. The method of any of paragraphs 1 through 65, further comprising the steps of extracting the carboxylic acid from any water and sugar after the reaction before it is recycled back into the reactor.

67. The method of any of paragraphs 1 through 66, further comprising the step of removing any soluble tars from the sugar or sugar acetates by precipitation into water or another co-solvent.

68. The method of any of paragraphs 1 through 66, further comprising the step of removing any soluble tars from the sugar or sugar acetates by extraction into an extraction solvent.

The following paragraphs also provide for various aspects of the present invention. In one embodiment, in a first paragraph (1), the present invention provides a method for making an HMF derivative, the method comprising the steps of:

mixing sugar with a carboxylic acid, alcohol, or ketone to form a mixture having less than 5000 ppm of water; and heating the mixture in the presence of a catalyst in a reactor to a temperature of from about 40° C. to about 220° C. to provide a composition comprising the HMF derivative and between 0% and about 1% solid char.

2. The method of paragraph 1, wherein the composition comprises levulinic acid.

3. The method of either of paragraphs 1 or 2, wherein the composition comprises HMF.

4. The method of any of paragraphs 1 through 3, wherein the HMF derivative is an HMF-ester.

5. The method of paragraph 4, wherein the HMF derivative is HMF-acetate.

6. The method of any of paragraphs 1 through 3, wherein the HMF derivative is an HMF-ether.

7. The method of any of paragraphs 1 through 6, wherein the sugar is high fructose corn syrup, sucrose or inulin.

8. The method of paragraph 7, wherein the high fructose corn syrup is HFCS-90, HFCS-42, or HMFCS-55.

9. The method of any of paragraphs 1 through 8, wherein the mixture contains less 2500 ppm of water.

10. The method of any of paragraphs 1 through 9, wherein the catalyst is a heterogeneous catalyst.

11. The method of paragraph 10, wherein the catalyst is a sulfonic acid ion exchange resin.

12. The method of paragraph 11, wherein the catalyst is selected from the group consisting of Amberlyst 15, Amberlyst 35, Amberlyst 70, Amberlyst BD20, Nafion NR50, Nafion SAC 13, or any combination thereof.

13. The method of any of paragraphs 1 through 12, wherein the catalyst is a first catalyst, further comprising a second catalyst in the mixture.

14. The method of paragraph 13, wherein the second catalyst is a homogeneous catalyst.

15. The method of paragraph 14, wherein the second catalyst is sulfuric acid.

16. The method of paragraph 15, wherein the sulfuric acid is less than about 5% by weight of the mixture.

17. The method of any of paragraphs 1 through 16, wherein the sugar and carboxylic acid, alcohol, or ketone are mixed together prior to introduction into the reactor.

18. The method of paragraph 17, wherein the sugar and carboxylic acid, alcohol, or ketone are heated to remove water prior to introduction into the reactor.

19. The method of any of paragraphs 1 through 18, the mixture further comprising a co-solvent.

20. The method of paragraph 19, wherein the co-solvent is a hydrocarbon that does not contain a heteroatom.

21. The method of paragraph 19, wherein the co-solvent is a hydrocarbon that contain a heteroatom.

22. The method of paragraph 20, wherein the co-solvent is cyclohexane.

23. The method of paragraph 20, wherein the co-solvent is DMSO.

24. The method of paragraph 20, wherein the co-solvent is toluene.

25. The method of paragraph 20, wherein the co-solvent is THF.

26. The method of any of paragraphs 19 through 25, wherein the co-solvent is between about 0.1 to about 95% by weight of the mixture.

27. The method of paragraph 26, wherein the co-solvent is between about 1 to about 90% by weight of the mixture.

28. The method of paragraph 26, wherein the co-solvent is between about 40 to about 80% by weight of the mixture.

29. The method of any of paragraphs 1 through 28, wherein the sugar is between about 0.1 to about 50% by weight of the mixture.

30. The method of paragraph 29, wherein the sugar is between about 0.2 to about 25% by weight of the mixture.

31. The method of paragraph 29, wherein the sugar is between about 5 to about 20% by weight of the mixture.

32. The method of any of paragraphs 1 through 31, wherein the carboxylic acid, alcohol or ketone is a carboxylic acid.

33. The method of paragraph 32, wherein the carboxylic acid is selected from the group consisting of acetic acid, formic acid, propionic acid, lactic acid, oxalic acid, butyric acid, levulinic acid, pyruvic acid, trifluoroacetic acid, trichloroacetic acid, benzoic acid, and combinations thereof.

34. The method of paragraph 33, wherein the carboxylic acid is acetic acid.

35. The method of any of paragraphs 1 through 31, wherein the carboxylic acid, alcohol or ketone is an alcohol.

36. The method of paragraph 35, wherein the alcohol is a C1-C18 alcohol.

37. The method of paragraph 36, wherein the alcohol is selected from the group consisting of methanol, ethanol, propanol, butanol, pentanol, iso-butanol, hexanol, octanol, 2-ethylhexanol, isopropanol, cyclohexanol, ethylene glycol, propane-diol, benzyl alcohol, trifluoroethanol, hexafluoroisopropanol, and mixtures thereof.

38. The method of any of paragraphs 1 through 31, wherein the carboxylic acid, alcohol or ketone is a ketone.

39. The method of paragraph 38, wherein the ketone is selected from the group consisting of methyl ethyl ketone, acetone, methyl-iso-butylketone, cyclohexanone, hexafluoroacetone, isophorone, and methyl-isoamyl ketone and mixtures thereof.

40. The method of paragraph 38, wherein the ketone is acetone.

41. The method of any of paragraph 1 through 40, wherein the carboxylic acid, alcohol, or ketone is between about 0.1 to about 99.9% by weight of the mixture.

42. The method of paragraph 41, wherein the carboxylic acid, alcohol or ketone is between about 1 to about 95% by weight of the mixture.

43. The method of paragraph 41, wherein the carboxylic acid, alcohol or ketone is between about 5 to about 90% by weight of the mixture.

44. The method of paragraph 41, wherein the carboxylic acid, alcohol or ketone is between about 10 to about 85% by weight of the mixture.

45. The method of any of paragraphs 1 through 44, wherein the carboxylic acid, alcohol or ketone and sugar each contain less than about 5000 ppm of water prior to mixing.

46. The method of paragraph 45 wherein the carboxylic acid, alcohol or ketone and sugar each contain less than about 1000 ppm of water prior to mixing.

47. The method of any of paragraphs 1 through 46, wherein the mixture is heated in the presence of a catalyst to a temperature of from about 40° C. to about 130° C.

48. The method of any of paragraphs 1 through 46, wherein the mixture is heated in the presence of a catalyst to a temperature of from about 60° C. to about 100° C.

49. The method of any of paragraphs 1 through 48, wherein the composition comprises sugar acetate, sugar ether, sugar ketals, or sugar acetonides.

50. The method of any of paragraphs 1 through 49, wherein the composition comprises soluble tars.

51. The method of any of paragraphs 1 through 50, wherein the composition comprises formic acid and/or formic acid esters.

52. The method of any of paragraphs 1 through 51, wherein the composition comprises levulinic acid esters.

53. The method of any of paragraphs 1 through 52, wherein the reactor is a batch reactor.

54. The method of any of paragraphs 1 through 52, wherein the reactor is a continuous addition batch reactor.

55. The method of any of paragraphs 1 through 52, wherein the reactor is a continuous stirred tank reactor.

56. The method of paragraph 55, wherein the reactor is a reactor system having a series of 2 or more continuous stirred tank reactors.

57. The method of paragraph 56, wherein the total amount of sugar is introduced in fractional amounts in each continuous stirred tank reactor.

58. The method of any of paragraphs 1 through 52 wherein the reactor is a plug flow reactor.

59. The method of paragraph 58, wherein the reactor is a reactor system having a series of 2 or more plug flow reactors.

60. The method of paragraph 59, wherein the total amount of sugar is introduced in fractional amounts in each plug flow reactor.

61. The method of any of paragraphs 55 through 60, wherein the reactor system is a combination of CSTRs and plug flow reactors.

62. The method of any of paragraphs 1 through 61, wherein the mixture has a residence time in the reactor between about 5 minutes and about 16 hours.

63. The method of any of paragraphs 1 through 61, wherein the mixture has a residence time in the reactor between about 10 minutes minute and about 12 hours.

64. The method of any of paragraphs 1 through 61, wherein the mixture has a residence time in the reactor between about 20 minutes and about 4 hours.

65. The method of any of paragraphs 1 through 64, wherein the sugar is added to the reactor at a rate such that the sugar content of the mixture remains less than or equal to about 5% by weight of the mixture during the entire reaction.

66. The method of any of paragraphs 1 through 65, wherein the reaction is greater than 50% selective to forming a combination of HMF-acetate, or HMF-ether, HMF, and LA and/or LA ester versus tar and char.

67. The method of any of paragraphs 1 through 65, wherein the reaction is greater than 60% selective to forming a combination of HMF-acetate, or HMF-ether, HMF, and LA and/or LA ester HMF, and LA versus tar and char.

68. The method of any of paragraphs 1 through 65, wherein the reaction is greater than 70% selective to forming a combination of HMF-acetate, or HMF-ether, HMF, and LA and/or LA ester HMF, and LA versus tar and char.

69. The method of any of paragraphs 1 through 65, wherein the reaction is greater than 80% selective to forming a combination of HMF-acetate, or HMF-ether, HMF, and LA and/or LA ester HMF, and LA versus tar and char.

70. The method of any of paragraphs 1 through 69, wherein the sugar and sugar acetate, sugar ether, or sugar acetonide conversion does not exceed 75% conversion during the reaction.

71. The method of any of paragraphs 1 through 69, wherein the sugar and sugar acetate, sugar ether, or sugar acetonide conversion does not exceed 90% conversion during the reaction.

72. The method of any of paragraphs 1 through 71, further comprising the step of removing water from the reactor or reactors during the reaction.

73. The method of any of paragraphs 1 through 72, further comprising recycling the HMF derivative formed during the reaction back to a reactor feed inlet for further reaction.

74. The method of any of paragraphs 1 through 73, further comprising recycling the levulinic acid formed during the reaction back to a reactor feed inlet for further reaction.

75. The method of any of paragraphs 1 through 74, further comprising reacting the HMF-derivative into a second product.

76. The method of paragraph 75, wherein the second product is furan dicarboxylic acid.

77. The method of paragraph 75, wherein the second product is levulinic acid.

78. The method of paragraph 77, wherein the levulinic acid is recycled back to a reactor feed inlet for further reaction.

79. The method of paragraph 77, further comprising reacting the levulinic acid into a third product.

80. The method of paragraph 79, wherein the third product is selected from the group consisting of succinic acid, suberic acid, gamma valero lactone, angelica lactone, methylene valero lactone, alkyl levulinates, levulinic ketals, diphenolic acid and combinations thereof.

81. The method of paragraph 80, wherein the third product is succinic acid.

82. The method of paragraph 80, wherein the third product is ethyl levulinate.

83. The method of paragraph 80, wherein the third product is methyl levulinate.

84. The method of paragraph 80, wherein the third product is a levulinic ketal.

85. The method of any of paragraphs 1 through 84, wherein the catalyst is a reusable or recyclable heterogeneous catalysts.

86. The method of paragraph 85, further comprising recharging the catalyst by washing the catalyst with water, alcohol, ketone, or carboxylic acid.

87. The method of any of paragraphs 1 through 86, further comprising hydrolyzing the sugar esters, sugar ethers, sugar acetonides, or sugar ketals with water.

88. The method of paragraph 87, further comprising recycling the sugar back to a reactor feed inlet for further reaction.

89. The method of paragraph 88, further comprising recycling the carboxylic acid, alcohol or ketone back to a reactor feed inlet for further reaction.

90. The method of any of paragraphs 1 through 89, further comprising isolating and recovering HMF-acetate or HMF-ether.

91. The method of any of paragraphs 1 through 90, further comprising isolating and recovering HMF.

92. The method of any of paragraphs 1 through 91, further comprising isolating and recovering LA or LA ester.

93. The method of any of paragraphs 1 through 92, further comprising isolating and recovering formic acid or FA ester.

94. The method of any of paragraphs 1 through 93, further comprising isolating and recovering furan dicarboxylic acid from a subsequent oxidation step.

95. The method of any of paragraphs 1 through 94, wherein the sugar comprises glucose, further comprising the step of isomerizing the glucose into fructose before it is recycled back into the reaction inlet.

96. The method of any of paragraphs 1 through 95, further comprising the steps of extracting the carboxylic acid, alcohol or ketone from any water and sugar after the reaction before it is recycled back into the reactor.

97. The method of any of paragraphs 1 through 96, further comprising the step of removing any soluble tars from the sugar, sugar acetates, sugar ethers, sugar acetonides, or sugar ketals by precipitation into water or another co-solvent.

98. The method of any of paragraphs 1 through 96, further comprising the step of removing any soluble tars from the sugar, sugar acetates, sugar ethers, sugar acetonides, or sugar ketals by extraction into an extraction solvent.

99. A method for making 5-methoxymethyl-2-furfural, the method comprising the steps of:
providing methanol;
providing high fructose corn syrup containing less than about 5000 ppm of water;
providing a co-solvent containing less than about 5000 ppm of water;
adding the methanol, the high fructose corn syrup, and the non-co-solvent to a reactor to form a reaction mixture; and
heating the reaction mixture in the presence of a heterogeneous catalyst at a temperature from about 40° C. to about 220° C. to provide a composition comprising 5-methoxymethyl-2-furfural and optionally sugar ethers.

100. A method for making 5-methoxy-2-furfural, the method comprising the steps of:
providing acetone;
providing high fructose corn syrup containing less than about 5000 ppm of water;
providing a co-solvent containing less than about 5000 ppm of water;
adding the acetone, the high fructose corn syrup, and the co-solvent to a reactor to form a reaction mixture; and
heating the reaction mixture in the presence of a heterogeneous catalyst at a temperature from about 40° C. to about 220° C. to provide a composition comprising 5-hydroxymethyl-2-furfural and optionally sugar acetonides.

The following paragraphs also provide for various aspects of the present invention. In one embodiment, in a first paragraph (1), the present invention provides a method for making an HMF derivative, the method comprising the steps of:
providing sugar;
providing a carboxylic acid, alcohol, or ketone;
combining the sugar with the carboxylic acid, alcohol, or ketone to form a mixture; and
heating the mixture in the presence of a catalyst in a reactor to a temperature of from about 40° C. to about 220° C. to provide a composition comprising the HMF derivative and between 0% and about 1% solid char.

2. A method for making an HMF derivative, the method comprising the steps of:
providing sugar;
providing a carboxylic acid, alcohol, or ketone;
providing a co-solvent that is a hydrocarbon that does not contain a heteroatom;
combining the sugar with the carboxylic acid, alcohol or ketone and the co-solvent to form a mixture; and
heating the mixture in the presence of a catalyst in a reactor to a temperature of from about 40° C. to about 220° C. to provide a composition comprising the HMF derivative.

3. The method of either of paragraphs 1 or 2, wherein the composition comprises HMF or levulinic acid.

4. The method of any of paragraphs 1 through 3, wherein the HMF derivative is an HMF-ester.

5. The method of paragraph 4, wherein the HMF derivative is HMF-acetate.

6. The method of any of paragraphs 1 through 3, wherein the HMF derivative is an HMF-ether.

7. The method of any of paragraphs 1 through 6, wherein the sugar is high fructose corn syrup, sucrose or inulin.

8. The method of paragraph 7, wherein the high fructose corn syrup is HFCS-90, HFCS-42, or HMFCS-55.

9. The method of any of paragraphs 1 through 8, wherein the mixture contains less 5000 ppm of water.

10. The method of any of paragraphs 1 through 9, wherein the catalyst is a heterogeneous catalyst.

11. The method of paragraph 10, wherein the catalyst is a sulfonic acid ion exchange resin.

12. The method of paragraph 11, wherein the catalyst is selected from the group consisting of Amberlyst 15, Amberlyst 35, Amberlyst 70, Amberlyst BD20, Nafion NR50, Nafion SAC 13, or any combination thereof.

13. The method of any of paragraphs 1 through 12, wherein the catalyst is a first catalyst, further comprising a second catalyst in the mixture.

14. The method of paragraph 13, wherein the second catalyst is a homogeneous catalyst.

15. The method of paragraph 14, wherein the second catalyst is sulfuric acid.

16. The method of paragraph 15, wherein the sulfuric acid is less than about 5% by weight of the mixture.

17. The method of any of paragraphs 1 through 16, wherein the sugar and carboxylic acid, alcohol, or ketone are mixed together prior to introduction into the reactor.

18. The method of paragraph 17, wherein the sugar and carboxylic acid, alcohol, or ketone are heated to remove water prior to introduction into the reactor.

19. The method of any of paragraphs 1 or 3 through 18, the mixture further comprising a co-solvent.

20. The method of paragraph 19, wherein the co-solvent is a hydrocarbon that does not contain a heteroatom.

21. The method of paragraph 19, wherein the co-solvent is a hydrocarbon that contain a heteroatom.

22. The method of either of paragraphs 2 or 20, wherein the co-solvent is cyclohexane.

23. The method of paragraph 21, wherein the co-solvent is DMSO.

24. The method of paragraph 21, wherein the co-solvent is toluene.

25. The method of paragraph 21, wherein the co-solvent is THF.

26. The method of any of paragraphs 2 or 19 through 25, wherein the co-solvent is between about 0.1 to about 95% by weight of the mixture.

27. The method of paragraph 26, wherein the co-solvent is between about 1 to about 90% by weight of the mixture.

28. The method of paragraph 26, wherein the co-solvent is between about 40 to about 80% by weight of the mixture.

29. The method of any of paragraphs 1 through 28, wherein the sugar is between about 0.1 to about 50% by weight of the mixture.

30. The method of paragraph 29, wherein the sugar is between about 0.2 to about 25% by weight of the mixture.

31. The method of paragraph 29, wherein the sugar is between about 5 to about 20% by weight of the mixture.

32. The method of any of paragraphs 1 through 31, wherein the carboxylic acid, alcohol or ketone is a carboxylic acid.

33. The method of paragraph 32, wherein the carboxylic acid is selected from the group consisting of acetic acid, formic acid, propionic acid, lactic acid, oxalic acid, butyric acid, levulinic acid, pyruvic acid, trifluoroacetic acid, trichloroacetic acid, benzoic acid, and combinations thereof.

34. The method of paragraph 33, wherein the carboxylic acid is acetic acid.

35. The method of any of paragraphs 1 through 31, wherein the carboxylic acid, alcohol or ketone is an alcohol.

36. The method of paragraph 35, wherein the alcohol is a C1-C18 alcohol.

37. The method of paragraph 36, wherein the alcohol is selected from the group consisting of methanol, ethanol, propanol, butanol, pentanol, iso-butanol, hexanol, octanol, 2-ethylhexanol, isopropanol, cyclohexanol, ethylene glycol, propane-diol, benzyl alcohol, trifluoroethanol, hexafluoroisopropanol, and mixtures thereof.

38. The method of any of paragraphs 1 through 31, wherein the carboxylic acid, alcohol or ketone is a ketone.

39. The method of paragraph 38, wherein the ketone is selected from the group consisting of methyl ethyl ketone, acetone, methyl-iso-butylketone, cyclohexanone, hexafluoroacetone, isophorone, and methyl-isoamyl ketone and mixtures thereof.

40. The method of paragraph 38, wherein the ketone is acetone.

41. The method of any of paragraph 1 through 40, wherein the carboxylic acid, alcohol, or ketone is between about 0.1 to about 99.9% by weight of the mixture.

42. The method of paragraph 41, wherein the carboxylic acid, alcohol or ketone is between about 1 to about 95% by weight of the mixture.

43. The method of paragraph 41, wherein the carboxylic acid, alcohol or ketone is between about 5 to about 90% by weight of the mixture.

44. The method of paragraph 41, wherein the carboxylic acid, alcohol or ketone is between about 10 to about 85% by weight of the mixture.

45. The method of any of paragraphs 1 through 44, wherein the carboxylic acid, alcohol or ketone and sugar each contain less than about 5000 ppm of water prior to mixing.

46. The method of paragraph 45 wherein the carboxylic acid, alcohol or ketone and sugar each contain less than about 1000 ppm of water prior to mixing.

47. The method of any of paragraphs 1 through 46, wherein the mixture is heated in the presence of a catalyst to a temperature of from about 40° C. to about 130° C.

48. The method of any of paragraphs 1 through 46, wherein the mixture is heated in the presence of a catalyst to a temperature of from about 60° C. to about 100° C.

49. The method of any of paragraphs 1 through 48, wherein the composition comprises sugar acetate, sugar ether, sugar ketals, or sugar acetonides.

50. The method of any of paragraphs 1 through 49, wherein the composition comprises soluble tars.

51. The method of any of paragraphs 1 through 50, wherein the composition comprises formic acid and/or formic acid esters.

52. The method of any of paragraphs 1 through 51, wherein the composition comprises levulinic acid esters.

53. The method of any of paragraphs 1 through 52, wherein the reactor is a batch reactor.

54. The method of any of paragraphs 1 through 52, wherein the reactor is a continuous addition batch reactor.

55. The method of any of paragraphs 1 through 52, wherein the reactor is a continuous stirred tank reactor.

56. The method of paragraph 55, wherein the reactor is a reactor system having a series of 2 or more continuous stirred tank reactors.

57. The method of paragraph 56, wherein the total amount of sugar is introduced in fractional amounts in each continuous stirred tank reactor.

58. The method of any of paragraphs 1 through 52 wherein the reactor is a plug flow reactor.

59. The method of paragraph 58, wherein the reactor is a reactor system having a series of 2 or more plug flow reactors.

60. The method of paragraph 59, wherein the total amount of sugar is introduced in fractional amounts in each plug flow reactor.

61. The method of any of paragraphs 55 through 60, wherein the reactor system is a combination of CSTRs and plug flow reactors.

62. The method of any of paragraphs 1 through 61, wherein the mixture has a residence time in the reactor between about 5 minutes and about 16 hours.

63. The method of any of paragraphs 1 through 61, wherein the mixture has a residence time in the reactor between about 10 minutes minute and about 12 hours.

64. The method of any of paragraphs 1 through 61, wherein the mixture has a residence time in the reactor between about 20 minutes and about 4 hours.

65. The method of any of paragraphs 1 through 64, wherein the sugar is added to the reactor at a rate such that the sugar content of the mixture remains less than or equal to about 5% by weight of the mixture during the entire reaction.

66. The method of any of paragraphs 1 through 65, wherein the reaction is greater than 50% selective to forming a combination of HMF-acetate, or HMF-ether, HMF, and LA and/or LA ester versus tar and char.

67. The method of any of paragraphs 1 through 65, wherein the reaction is greater than 60% selective to forming a combination of HMF-acetate, or HMF-ether, HMF, and LA and/or LA ester HMF, and LA versus tar and char.

68. The method of any of paragraphs 1 through 65, wherein the reaction is greater than 70% selective to forming a combination of HMF-acetate, or HMF-ether, HMF, and LA and/or LA ester HMF, and LA versus tar and char.

69. The method of any of paragraphs 1 through 65, wherein the reaction is greater than 80% selective to forming a combination of HMF-acetate, or HMF-ether, HMF, and LA and/or LA ester HMF, and LA versus tar and char.

70. The method of any of paragraphs 1 through 69, wherein the sugar and sugar acetate, sugar ether, or sugar acetonide conversion does not exceed 75% conversion during the reaction.

71. The method of any of paragraphs 1 through 69, wherein the sugar and sugar acetate, sugar ether, or sugar acetonide conversion does not exceed 90% conversion during the reaction.

72. The method of any of paragraphs 1 through 71, further comprising the step of removing water from the reactor or reactors during the reaction.

73. The method of any of paragraphs 1 through 72, further comprising recycling the HMF derivative formed during the reaction back to a reactor feed inlet for further reaction.

74. The method of any of paragraphs 1 through 73, further comprising recycling the levulinic acid formed during the reaction back to a reactor feed inlet for further reaction.

75. The method of any of paragraphs 1 through 74, further comprising reacting the HMF-derivative into a second product.

76. The method of paragraph 75, wherein the second product is furan dicarboxylic acid.

77. The method of paragraph 75, wherein the second product is levulinic acid.

78. The method of paragraph 77, wherein the levulinic acid is recycled back to a reactor feed inlet for further reaction.

79. The method of paragraph 77, further comprising reacting the levulinic acid into a third product.

80. The method of paragraph 79, wherein the third product is selected from the group consisting of succinic acid, suberic acid, gamma valero lactone, angelica lactone, methylene valero lactone, alkyl levulinates, levulinic ketals, diphenolic acid and combinations thereof.

81. The method of paragraph 80, wherein the third product is succinic acid.

82. The method of paragraph 80, wherein the third product is ethyl levulinate.

83. The method of paragraph 80, wherein the third product is methyl levulinate.

84. The method of paragraph 80, wherein the third product is a levulinic ketal.

85. The method of any of paragraphs 1 through 84, wherein the catalyst is a reusable or recyclable heterogeneous catalysts.

86. The method of paragraph 85, further comprising recharging the catalyst by washing the catalyst with water, alcohol, ketone, or carboxylic acid.

87. The method of any of paragraphs 1 through 86, further comprising hydrolyzing the sugar esters, sugar ethers, sugar acetonides, or sugar ketals with water.

88. The method of paragraph 87, further comprising recycling the sugar back to a reactor feed inlet for further reaction.

89. The method of paragraph 88, further comprising recycling the carboxylic acid, alcohol or ketone back to a reactor feed inlet for further reaction.

90. The method of any of paragraphs 1 through 89, further comprising isolating and recovering HMF-acetate or HMF-ether.

91. The method of any of paragraphs 1 through 90, further comprising isolating and recovering HMF.

92. The method of any of paragraphs 1 through 91, further comprising isolating and recovering LA or LA ester.

93. The method of any of paragraphs 1 through 92, further comprising isolating and recovering formic acid or FA ester.

94. The method of any of paragraphs 1 through 93, further comprising isolating and recovering furan dicarboxylic acid from a subsequent oxidation step.

95. The method of any of paragraphs 1 through 94, wherein the sugar comprises glucose, further comprising the step of isomerizing the glucose into fructose before it is recycled back into the reaction inlet.

96. The method of any of paragraphs 1 through 95, further comprising the steps of extracting the carboxylic acid, alcohol or ketone from any water and sugar after the reaction before it is recycled back into the reactor.

97. The method of any of paragraphs 1 through 96, further comprising the step of removing any soluble tars from the sugar, sugar acetates, sugar ethers, sugar acetonides, or sugar ketals by precipitation into water or another co-solvent.

98. The method of any of paragraphs 1 through 96, further comprising the step of removing any soluble tars from the sugar, sugar acetates, sugar ethers, sugar acetonides, or sugar ketals by extraction into an extraction solvent.

The following non-limiting examples further illustrate various embodiments as described herein.

EXAMPLES

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Example 1

6.758 g Fructose, 0.768 g Glucose, and 25.59 g glacial acetic acid was charged into a 100 ml beaker. The beaker was placed on a hot plate and, using minimal heat, the sugar was dissolved in the acetic acid. Once the sugar was dissolved and the mixture was cool it was charged into a 60 ml syringe. The rate of the syringe pump was set so that the sugar/acetic acid solution would be fed into a round bottom flask over the course of two hours. 12.05 g Amberlyst® 35 (A35), 45.08 g cyclohexane, and 72.01 g glacial acetic acid was charged into a 250 ml round bottom flask. The round bottom flask was situated on a heating mantle on a stir plate and equipped with a magnetic stir bar, thermocouple, condenser and syringe pump inlet. Once the mixture was boiling, which was approximately 65° C., the syringe pump was turned on to start feeding the sugar solution into the round bottom flask. Once all of the sugar solution had been added to the round bottom flask the mixture was heated at the same temperature for one hour (cook step) and the mixture was sampled. Samples were analyzed by GC, LC, and LC-MS. The conditions and final composition data is shown in Table 1. The selectivity and conversion data is shown in Table 2.

Example 2

The same reaction was performed as Example 1 but this time without the cyclohexane. The conditions and final composition data is shown in Table 1. The selectivity and conversion data is shown in Table 2.

TABLE 1

Composition Data for Examples 1-2.

| Example | Time (min) | Temp ° C. | % LA (GC) | % FA (LC) | % HMF (GC) | % AMF (GC) | % Glucose (LC) | % Fructose (LC) | % Sugar Acetates (LC-MS) |
|---|---|---|---|---|---|---|---|---|---|
| 1 | 180 | 65.3 | 0.15 | 0.11 | 0.18 | 2.10 | 0.00 | 0.00 | 4.2 |
| 2 | 180 | 65.3 | 0.03 | 0.05 | 0.11 | 1.31 | 0.00 | 0.00 | 5.8 |

TABLE 2

Selectivity and Conversion Data for Examples 1-2.

| Example | % AMF Selectivity | % HMF Selectivity | % LA Selectivity | % Sugar + Sugar Acetate Conversion |
|---|---|---|---|---|
| 1 | 83 | 9 | 8 | 52 |
| 2 | 79 | 9 | 3 | 34 |

As can be seen in these 2 examples, the addition of sugar into glacial acetic acid results in a high selectivity reaction (>90%). Also, Example 1 showed that when cyclohexane was added as a co-solvent in the reaction. This resulted in much higher % selectivity for AMF and LA.

Example 3

A 100 mL 3-neck round bottom flask was charged with 58 g glacial acetic acid, 3.5 g ethyl acetate, 5.6 g A35 catalyst, and 2.7 g HFCS-90 (Cornsweet® 90 ADM, Inc). The flask was equipped with an overhead mixer, thermocouple, and a condenser. The contents of the flask were heated to 100° C. using a heating mantle. After 2 hours, a sample was taken for analytical testing. The reaction mixture was allowed to cool to ambient temperature. The sample was analyzed by LC and GC-FID for levulinic acid, formic acid, HMF, AMF, and char. Results are shown in Table 3.

Examples 4-7

Examples 4-7 were performed under the same procedure as Example 3 with changes to the temperature, catalyst type, and type of co-solvent used as shown in Table 3.

In Examples 3-7, there was no appearance of char under these operating conditions. Also, the amount of levulinic and formic acid could be increased by the addition of ethyl acetate or sulfolane. In Example 7, the sulfuric acid catalyst (0.5 wt %) produced lower yields of LA, FA, HMF, and AMF during the 2 h reaction.

Example 8

A 500 mL 4-neck round bottom flask was charged with 237.2 g glacial acetic acid and 24.2 g (8%) A35 catalyst. The flask was equipped with an overhead mixer, thermocouple, condenser, and a syringe pump. The contents of the flask were heated to 90° C. using a heating mantle. Once at temperature, 38.9 g HFCS-90 was slowly injected into the reactor, using the syringe pump, over a 1 hour time period (Feed Time). Once the sugar was completely injected, the reaction was kept at 90° C. for an additional 1 hour (Cook Time). The reaction mixture was then allowed to cool to ambient temperature. The samples taken for testing were analyzed by LC, GPC, and GC-FID for analysis of the composition. Results are shown in Table 4.

Examples 9-12

Examples 9-12 were performed under the same procedure as Example 8 with changes to the concentration of sugar used, temperature of reaction, Feed Time, and Cook Time as shown in Table 4.

TABLE 3

| Example | Temp (° C.) | Catalyst Type | wt % Catalyst | Solvent | wt % Sugar | % LA | % FA | % HMF | % AMF | % Char |
|---|---|---|---|---|---|---|---|---|---|---|
| Ex. 3 | 100 | A35 | 8 | Acetic Acid + 5% Ethyl Acetate | 3 | 0.2 | 0.2 | 0.1 | 1.0 | 0.0 |
| Ex. 4 | 80 | A35 | 8 | Acetic Acid | 3 | 0.03 | 0.1 | 0.1 | 1.2 | 0.0 |
| Ex. 5 | 80 | A35 | 8 | Sulfolane | 3 | 0.9 | 0.4 | 0.2 | 0.0 | 0.0 |
| Ex. 6 | 80 | A35 | 8 | Ethyl Acetate | 3 | 0.00 | 0.03 | 0.1 | 1.1 | 0.0 |
| Ex. 7 | 80 | $H_2SO_4$ | 0.5 | Acetic Acid | 3 | 0.00 | 0.02 | 0.03 | 0.6 | 0.0 |

TABLE 4

| Ex. | Temp (° C.) | wt % Sugar | Feed Time (h) | Cook Time (h) | % Sugar + Sugar acetate Conversion | % HMF Selectivity | % AMF Selectivity | % LA Selectivity |
|---|---|---|---|---|---|---|---|---|
| Ex. 8 | 90 | 10 | 1 | 1 | 64 | 16 | 50 | 6 |
| Ex. 9 | 110 | 10 | 2 | 0 | 81 | 12 | 34 | 10 |
| Ex. 10 | 90 | 20 | 2 | 0 | 43 | 31 | 40 | 4.5 |
| Ex. 11 | 90 | 20 | 1 | 0 | 30 | 33 | 41 | 2 |
| Ex. 12 | 100 | 15 | 1.5 | 0 | 60 | 25 | 41 | 5 |

The data in Table 4 shows that reactions below 110° C. produce a much higher selectivity for HMF and AMF, and the reaction at 110° C. produces higher LA.

Example 13

A 1 L 4-neck round bottom flask was charged with 333.37 g glacial acetic acid and 32.2 g (8%) A35 catalyst. The flask was equipped with an overhead mixer, thermocouple, condenser, and a syringe pump. The contents of the flask were heated to 70° C. using a heating mantle. Once at temperature, 66.71 g of a solution containing 15 wt % fructose and 1.67 wt % glucose dissolved in glacial acetic acid was injected into the reactor, using the syringe pump, over a 1 hour time period (Feed Time). Once the sugar was completely injected, the reaction was raised to 90° C. for an additional 1 hour (Cook Time). The reaction mixture was allowed to cool to ambient temperature. A sample was taken for testing and was analyzed by LC, GPC, and GC-FID for composition. Analysis showed the reaction went to 40% conversion and the selectivities were 85% AMF, 5% LA, and 7% HMF. This reaction demonstrates that the absence of water in the sugar feed and the low temperature of the reaction gives rise to high product selectivities (97% combined product selectivity for AMF, LA, and HMF).

Example 14

A 250 mL 3-neck round bottom flask was charged with 13.9 g glacial acetic acid, 30.0 g of DMSO, and 4.2 g (8 wt %) A35 catalyst. The flask was equipped with a magnetic stirrer, thermocouple, condenser, and a syringe pump. The contents of the flask were heated to 105° C. using a heating mantle and stirred. Once at 105° C., 8.8 g of a solution containing 15 wt % fructose and 1.7 wt % glucose dissolved in glacial acetic acid was injected into the reactor, using a syringe pump, over a 1 hour time period (Feed Time). Once the sugar was completely injected, the reaction was heated for an additional 2 h (Cook Time). The reaction mixture was allowed to cool to ambient temperature. A sample was taken for testing and was analyzed by LC, GPC, and GC-FID. The data is shown below in Table 5.

Examples 15-18

Examples 15-18 were performed similarly to Example 14, except with changes to the temperature, cook time, and type of co-solvent used. The data is shown below in Table 5.

TABLE 5

| Ex. | Solvent System (Initial wt:wt ratio) | Phase Behavior | Final System (wt:wt ratio of solvents in biphasic reaction) | Temp (° C.) | Cook Time (h) | % Sugar Acetates | % Sugar and Sugar Acetate Conversion | HMF Selectivity | AMF Selectivity | LA Selectivity |
|---|---|---|---|---|---|---|---|---|---|---|
| Ex. 14 | 66:34 DMSO:AcOH | 1 Phase | 1 phase | 105 | 2 | 2.9 | 59 | 82 | 13 | 1 |
| Ex. 15 | 60:40 Toluene:AcOH | 1 Phase | 1 phase | 64.5 | 5 | 1.4 | 85 | 8 | 53 | 11.5 |
| Ex. 16 | 60:40 Mineral oil:AcOH | 2 Phases | 69:31 Mineral oil:AcOH | 64.5 | 5 | 7.9 | 67 | 8 | 42 | 11 |
| Ex. 17 | 60:40 n-hexane:AcOH | 2 Phases | 78:22 n-hexane:AcOH | 64.5 | 5 | 12.7 | 66 | 7 | 32 | 8 |
| Ex. 18 | 60:40 cyclohexane:AcOH | 2 Phases | 49:51 cyclohexane:AcOH | 64.5 | 5 | 3.3 | 76 | 7 | 53 | 36 |

As can be seen in Table 5, the use of a co-solvent greatly affects the selectivity of the products in the reaction. The use of cyclohexane provides a much larger quantity of LA compared to the other co-solvents. In all examples, no solid char was formed.

Examples 19-21

Example 18 was repeated at 65° C., except after the sugar feed step, the cyclohexane solvent phase was removed via pipette before the cook step at 70° C. Results are shown in Table 6.

TABLE 6

| Example | Temp (° C.) | Cook Time (h) | % Sugar Acetates in AcOH Phase | % Sugar and Sugar Acetate Conversion | HMF Selectivity | AMF Selectivity | LA Selectivity |
|---|---|---|---|---|---|---|---|
| Ex. 19 | 70 | 4 | 4 | 67.5 | 13 | 61 | 23 |
| Ex. 20 | 70 | 8 | 3.3 | 73 | 9 | 49 | 34 |
| Ex. 21 | 70 | 11.2 | 3.1 | 75 | 7.5 | 40 | 39.5 |

As can be seen in Table 6, as the overall percent conversion goes up, the AMF Selectivity goes down and the LA Selectivity goes up considerably. The overall selectivity of each of these Examples was >85%, and there is no solid char that was formed.

Example 22

A 3 wt % sugar solution was prepared by dissolving 108 g of fructose and 12 g of glucose into 3880 g of glacial acetic acid. The 3 wt % sugar in acetic acid solution contained less than 2000 ppm of water. This solution was pumped at 50 mL/hour via peristaltic pump into a plug-flow reactor (PFR) containing a packed bed of 14 g of A35 catalyst in a 30 mL PFR. The 3 wt % sugar solution was pumped for >24 h and samples were taken from the effluent. The compositional analysis of the furanic products is shown in Table 7. The conversion of sugar into HMF and AMF was relatively consistent, and the selectivity of the reaction was high. No solid char was formed, and the main side-products were sugar acetates, which can be hydrolyzed and converted back into sugar, so the sugar acetate side-products should not be considered as by-product yield losses.

TABLE 7

| Time (h) | % HMF in Effluent | % AMF in Effluent |
| --- | --- | --- |
| 1.5 | 0.04 | 0.9 |
| 3 | 0.05 | 0.9 |
| 5 | 0.04 | 1.0 |
| 22 | 0.06 | 1.1 |
| 26.5 | 0.07 | 1.1 |
| 29.5 | 0.08 | 1.1 |
| 34.5 | 0.10 | 1.0 |

Example 23

46.5 g of deionized water (DI) was placed into a 100 mL round bottom flask. 2.5 g of Amberlyst 15 catalyst was placed into the flask followed by 4.4 g of DI water. The flask was heated to reflux and mixed with a magnetic stirrer. 0.714 g of 5-acetoxymethyl-2 furaldehyde (AMF) and 3.286 g of glacial acetic acid was mixed into a solution in a 20 mL vial. 4 g of the solution in the vial was added into a 10 mL plastic syringe and the syringe was attached to a syringe pump that delivered the solution into the round bottom flask at a rate of 0.067 mL/min. The solution in the syringe pump finished adding after 1 h. The reaction was cooked for an additional 3 h and 25 min at reflux (98.4-98.5° C.). The final composition showed 0.01% AMF, 0.83 wt % HMF, and 0.12% LA. The combined % selectivity to LA and HMF was 99.8%, indicative of a highly selective reaction. No solid char was formed in the reaction.

Example 24

A 1 wt % sugar solution was prepared by dissolving 36 g of fructose and 4 g of glucose into 3960 g of glacial acetic acid. The 1 wt % sugar in acetic acid solution contained less than 2000 ppm of water. This solution was pumped at 50 mL/hour via peristaltic pump into a plug-flow reactor (PFR) containing a packed bed of 13.5 g of A35 catalyst in a 30 mL PFR at 60° C. Approximately every 24 h, the 1 wt % sugar feed was halted, and the PFR was washed with deionized (DI) water at 60° C. for 1 h. After 1 h of flushing with DI water, the 1 wt % sugar feed was switched to flow through the PFR at 50 mL/hour and 60° C. The 1 wt % sugar solution was pumped for >220 h and samples were taken from the effluent. The compositional analysis of the products is shown in Table 8. The conversion of sugar into LA, HMF, AMF was relatively consistent, and the selectivity of the reaction was high. No solid char was formed, and the main side-products were sugar acetates, which can be hydrolyzed and converted back into sugar, so the sugar acetate side-products should not be considered as by-product yield losses.

TABLE 8

| Time (h) | % LA (GC) | % HMF (GC) | % AMF (GC) | % Sugar Acetates (GPC) |
| --- | --- | --- | --- | --- |
| 2.0 | 0.00 | 0.01 | 0.18 | 0.90 |
| 4.0 | 0.01 | 0.00 | 0.20 | 0.83 |
| 5.8 | 0.00 | 0.01 | 0.20 | 0.81 |
| 9.0 | 0.00 | 0.00 | 0.19 | 0.82 |
| 22.0 | 0.00 | 0.00 | 0.19 | 0.79 |
| 25.0 | 0.00 | 0.02 | 0.17 | 0.94 |
| 27.0 | 0.00 | 0.01 | 0.20 | 0.81 |
| 29.0 | 0.00 | 0.00 | 0.20 | 0.80 |
| 31.8 | 0.00 | 0.00 | 0.20 | 0.79 |
| 45.0 | 0.00 | 0.01 | 0.21 | 0.77 |
| 48.0 | 0.00 | 0.01 | 0.19 | 0.86 |
| 50.0 | 0.00 | 0.01 | 0.21 | 0.79 |
| 51.5 | 0.00 | 0.01 | 0.22 | 0.78 |
| 55.8 | 0.00 | 0.00 | 0.21 | 0.77 |
| 68.5 | 0.00 | 0.00 | 0.22 | 0.75 |
| 71.0 | 0.01 | 0.03 | 0.19 | 0.89 |
| 73.0 | 0.01 | 0.01 | 0.22 | 0.77 |
| 74.5 | 0.01 | 0.01 | 0.22 | 0.76 |
| 77.8 | 0.01 | 0.01 | 0.23 | 0.75 |
| 91.0 | 0.01 | 0.02 | 0.25 | 0.75 |
| 94.0 | 0.01 | 0.01 | 0.20 | 0.77 |
| 114.0 | 0.01 | 0.01 | 0.21 | 0.76 |
| 117.0 | 0.00 | 0.01 | 0.19 | 0.83 |
| 120.0 | 0.01 | 0.01 | 0.21 | 0.78 |
| 124.5 | 0.01 | 0.01 | 0.21 | 0.78 |
| 136.0 | 0.00 | 0.01 | 0.21 | 0.78 |
| 141.5 | 0.01 | 0.01 | 0.18 | 0.76 |
| 146.0 | 0.01 | 0.01 | 0.18 | 0.76 |
| 160.0 | 0.00 | 0.01 | 0.19 | 0.76 |
| 170.0 | 0.01 | 0.01 | 0.19 | 0.72 |
| 186.0 | 0.00 | 0.01 | 0.19 | 0.73 |
| 192.5 | 0.01 | 0.02 | 0.20 | 0.72 |
| 209.0 | 0.01 | 0.01 | 0.20 | 0.74 |
| 215.5 | 0.01 | 0.01 | 0.20 | 0.74 |
| 226.5 | 0.01 | 0.01 | 0.20 | 0.74 |

Example 25

A 1 wt % sugar solution was prepared by dissolving 36 g of fructose and 4 g of glucose into 3168 g of glacial acetic acid and 792 g of cyclohexane. The 1 wt % sugar in acetic acid/cyclochexane solution contained less than 2000 ppm of water. This solution was pumped at 50 mL/hour via peristaltic pump into a plug-flow reactor (PFR) containing a packed bed of 13.5 g of A35 catalyst in a 30 mL PFR at 60° C. Approximately every 24 h, the 1 wt % sugar feed was halted, and the PFR was washed with deionized (DI) water at 60° C. for 1 h. After 1 h of flushing with DI water, the 1 wt % sugar feed was switched to flow through the PFR at 50 mL/hour and 60° C. The 1 wt % sugar solution was pumped for 75 h and samples were taken from the effluent. The compositional analysis of the products is shown in Table 9. The conversion of sugar into LA, HMF, AMF was relatively consistent, and the selectivity of the reaction was high. No solid char was formed, and the main side-products were sugar acetates, which can be hydrolyzed and converted back into sugar, so the sugar acetate side-products should not be considered as by-product yield losses.

TABLE 9

| Time (h) | % LA (GC) | % HMF (GC) | % AMF (GC) | % Sugar Acetates (GPC) |
|---|---|---|---|---|
| 1.5 | 0.01 | 0.01 | 0.19 | 0.69 |
| 4.5 | 0.01 | 0.01 | 0.20 | 0.64 |
| 18.5 | 0.01 | 0.00 | 0.20 | 0.63 |
| 28.5 | 0.00 | 0.01 | 0.22 | 0.67 |
| 34.5 | 0.01 | 0.01 | 0.22 | 0.61 |
| 41 | 0.01 | 0.01 | 0.20 | 0.66 |
| 57.5 | 0.01 | 0.00 | 0.23 | 0.60 |
| 64 | 0.01 | 0.01 | 0.23 | 0.62 |
| 75 | 0.01 | 0.01 | 0.24 | 0.61 |

Example 26

A 1 wt % sugar solution was prepared by dissolving 36 g of fructose and 4 g of glucose into 3168 g of glacial acetic acid and 792 g of cyclohexane. The 1 wt % sugar in acetic acid/cyclohexane solution contained less than 2000 ppm of water. This solution was pumped at 50 mL/hour via peristaltic pump into a plug-flow reactor (PFR) containing a packed bed of 13.5 g of A35 catalyst in a 30 mL PFR at 50° C. Approximately every 24 h, the 1 wt % sugar feed was halted, and the PFR was washed with deionized (DI) water at 50° C. for 1 h. After 1 h of flushing with DI water, the 1 wt % sugar feed was switched to flow through the PFR at 50 mL/hour and 50° C. The 1 wt % sugar solution was pumped for 75 h and samples were taken from the effluent. The compositional analysis of the products is shown in Table 10. The conversion of sugar into LA, HMF, AMF was relatively consistent, and the selectivity of the reaction was high. No solid char was formed, and the main side-products were sugar acetates, which can be hydrolyzed and converted back into sugar, so the sugar acetate side-products should not be considered as by-product yield losses.

TABLE 10

| Time (h) | % LA (GC) | % HMF (GC) | % AMF (GC) | % Sugar Acetates (GPC) |
|---|---|---|---|---|
| 1.5 | 0.00 | 0.00 | 0.14 | 0.81 |
| 4.5 | 0.00 | 0.00 | 0.18 | 0.68 |
| 18.5 | 0.00 | 0.01 | 0.18 | 0.68 |
| 28.5 | 0.00 | 0.00 | 0.13 | 0.77 |
| 34.5 | 0.00 | 0.01 | 0.14 | 0.78 |
| 41.0 | 0.00 | 0.01 | 0.13 | 0.80 |
| 57.5 | 0.00 | 0.00 | 0.14 | 0.79 |
| 64.0 | 0.00 | 0.01 | 0.14 | 0.79 |
| 75.0 | 0.00 | 0.00 | 0.15 | 0.79 |

Example 27

A 35 wt % "sugar solution" in 65 wt % glacial acetic acid was made in order to target a total of 5 wt % sugar fed into the reaction kettle. The "sugar solution" composition was 90 wt % fructose and 10 wt % glucose. 460 g of glacial acetic acid & 8 wt % A35 catalyst was charged into a 1000 mL 3-neck round bottom flask. The flask was equipped with a magnetic stir bar, thermocouple and attached to a lab distillation column with condenser attached above the reflux/take off adaptor. The contents of the flask were heated to 60° C. using a heating mantle pulling a vacuum of 90 mmHg to dry the mixture to desired concentration of <5000 ppm water (Actual measurement of mixture=2085 ppm $H_2O$). Overhead material of acetic acid and water was condensed and collected utilizing a magnetic reflux/take off timer. The temperature in the reaction kettle was adjusted to 86-89° C. with a vacuum of 450 mm Hg, and the "sugar solution" was added into the reaction kettle via vacuum-rated addition funnel at approximately 0.58 mLs/minute of over 2 h into the reaction kettle. Samples were pulled at 15 minute intervals. The magnetic reflux/take off timer on the lab distillation column was adjusted to ensure the overhead temperature did not get too hot. Upon completion of the 2 hour sugar addition a 75 min cook step was performed with a sample pulled at 15 minutes, 45 minutes, and 75 minutes. Once the experiment was complete all samples taken for testing were analyzed by GC, GPC & HPLC for levulinic acid, formic acid, HMF, AMF, and sugar acetates. The results are shown below in Table 11. There was no solid char observed during the reaction. There was no glucose or fructose observed in any of the samples.

TABLE 11

| Time (h) | % LA (GC) | % FA (LC) | % HMF (GC) | % AMF (GC) | Sugar-Acetates (GPC) |
|---|---|---|---|---|---|
| 15 | 0 | 0 | 0 | 0.09 | 0.42 |
| 30 | 0 | 0 | 0 | 0.41 | 0.92 |
| 45 | 0 | 0 | 0 | 0.7 | 1.2 |
| 60 | 0 | 0.01 | 0 | 1.04 | 1.31 |
| 75 | 0.03 | 0.02 | 0.01 | 1.18 | 1.42 |
| 90 | 0.04 | 0.03 | 0.02 | 1.48 | 1.85 |
| 105 | 0.05 | 0.03 | 0.02 | 1.8 | 2.2 |
| 120 | 0.06 | 0.03 | 0.03 | 1.89 | 2.27 |
| 135 | 0.07 | 0.04 | 0.02 | 1.94 | 2.44 |
| 165 | 0.09 | 0.03 | 0 | 2.23 | 2.46 |
| 195 | 0.1 | 0.01 | 0 | 2.32 | 2.51 |

Example 28

21.54 g of glacial acetic acid. 5.63 g of Amberlyst 15 catalyst was placed into a 100 mL round bottom flask followed by 1.44 g of DI water and 42.12 g of cyclohexane. The flask was heated to reflux at 65° C. and mixed with a magnetic stirrer. Into a 20 mL vial, was prepared a mixture of 1.407 g of AMF and 3.28 g of glacial acetic acid. The solution in the vial was transferred into a 10 mL plastic syringe and the syringe was attached to a syringe pump that delivered the solution into the round bottom flask over 1 h. The reaction was cooked for an additional 4 h at 65° C. The final composition in the polar phase showed 4.5 wt % AMF, 0.46 wt % HMF, and 0.32 wt % LA. The final composition in the non-polar phase was 0.04 wt % LA, 0.02 wt % HMF, and 0.04 wt % AMF. No solid char was formed in the reaction.

Example 29

Into a 100 mL round bottom flask was placed 16.34 g of glacial acetic acid. 5.61 g of Amberlyst 15 catalyst was placed into the flask followed by 2.81 g of DI water and 39.23 g of cyclohexane. The flask was heated to reflux at 65° C. and mixed with a magnetic stirrer. Into a 20 mL vial, was prepared a mixture of 3.510 g of AMF and 8.18 g of glacial acetic acid. The solution in the vial was transferred into a 25 mL plastic syringe and the syringe was attached to a syringe pump that delivered the solution into the round bottom flask over 1 h. The reaction was cooked for an additional 4 h at 65° C. The final composition in the polar phase showed 8.56 wt % AMF, 2.41 wt % HMF, and 0.43 wt % LA. The final composition in the non-polar phase was 0.01 wt % LA, 0.02 wt % HMF, and 0.28 wt % AMF. No solid char was formed in the reaction.

Example 30

A 250 mL 3-neck round bottom flask is charged with 13.9 g anhydrous methanol, 30.0 g of cyclohexane, and 4.2 g (8 wt %) Amberlyst 15 catalyst. All reagents have a combined water amount of less than 5000 ppm water. The flask is equipped with a magnetic stirrer, thermocouple, condenser, and a syringe pump. The contents of the flask are heated to 60° C. using a heating mantle and stirred. Once at 60° C., 8.8 g of a solution containing 15 wt % fructose and 1.7 wt % glucose dissolved/dispersed in anhydrous methanol (<5000 ppm water total) is injected into the reactor, using a syringe pump, over a 1 hour time period (Feed Time). Once the sugar is completely injected, the reaction is heated for an additional 2 h (Cook Time). The reaction mixture is allowed to cool to ambient temperature. A sample is taken for testing and is analyzed by LC, GPC, and GC-FID. The data shows the production of 5-methoxymethyl-2-furaldehyde, HMF, LA, FA, methyl formate, and methyl levulinate in high total product selectivity. Sugar ethers are also formed. Little to no solids are observed.

Example 31

A 250 mL 3-neck round bottom flask is charged with 13.9 g anhydrous ethanol, 30.0 g of cyclohexane, and 4.2 g (8 wt %) Amberlyst 15 catalyst. All reagents have a combined water amount of less than 5000 ppm water. The flask is equipped with a magnetic stirrer, thermocouple, condenser, and a syringe pump. The contents of the flask are heated to 60° C. using a heating mantle and stirred. Once at 60° C., 8.8 g of a solution containing 15 wt % fructose and 1.7 wt % glucose dissolved/dispersed in anhydrous ethanol (<5000 ppm water total) is injected into the reactor, using a syringe pump, over a 1 hour time period (Feed Time). Once the sugar is completely injected, the reaction is heated for an additional 2 h (Cook Time). The reaction mixture is allowed to cool to ambient temperature. A sample is taken for testing and is analyzed by LC, GPC, and GC-FID. The data shows the production of 5-methoxymethyl-2-furaldehyde, HMF, LA, FA, ethyl formate, and ethyl levulinate in high total product selectivity. Sugar ethers are also formed. Little to no solids are observed.

Example 32

A 250 mL 3-neck round bottom flask is charged with 13.9 g anhydrous acetone, 30.0 g of cyclohexane, and 4.2 g (8 wt %) Amberlyst 15 catalyst. All reagents have a combined water amount of less than 5000 ppm water. The flask is equipped with a magnetic stirrer, thermocouple, condenser, and a syringe pump. The contents of the flask are heated to 60° C. using a heating mantle and stirred. Once at 60° C., 8.8 g of a solution containing 15 wt % fructose and 1.7 wt % glucose dissolved (dispersed) in anhydrous acetone (<5000 ppm water total) is injected into the reactor, using a syringe pump, over a 1 hour time period (Feed Time). Once the sugar is completely injected, the reaction is heated for an additional 2 h (Cook Time). The reaction mixture is allowed to cool to ambient temperature. A sample is taken for testing and is analyzed by LC, GPC, and GC-FID. The data shows the production of HMF, FA and LA. Sugar acetonides are also formed. Little to no solids are observed.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A method for making an HMF derivative, the method comprising the steps of:
providing sugar;
providing a carboxylic acid, alcohol, or ketone;
combining the sugar with the carboxylic acid, alcohol, or ketone to form a mixture; and
heating the mixture in the presence of a catalyst in a reactor to a temperature of from about 40° C. to about 220° C. to provide a composition comprising the HMF derivative and between 0% and about 1% solid char.

2. The method of claim 1, wherein the composition comprises HMF or levulinic acid.

3. The method of claim 1, wherein the sugar is high fructose corn syrup, sucrose or inulin.

4. The method of claim 1, wherein the catalyst is a heterogeneous catalyst.

5. The method of claim 1, the mixture further comprising a co-solvent.

6. The method of claim 5, wherein the co-solvent is a hydrocarbon that contain a heteroatom.

7. The method of claim 6, wherein the co-solvent is cyclohexane, DMSO, toluene, or THF.

8. The method of claim 1, wherein the co-solvent is between about 0.1 to about 95% by weight of the mixture.

9. The method of claim 1, wherein the sugar is between about 0.1 to about 50% by weight of the mixture.

10. The method of claim 1, wherein the carboxylic acid, alcohol, or ketone is between about 0.1 to about 99.9% by weight of the mixture.

11. The method of claim 1, wherein the carboxylic acid, alcohol or ketone and sugar each contain less than about 5000 ppm of water prior to mixing.

12. The method of claim 1, wherein the mixture is heated in the presence of a catalyst to a temperature of from about 40° C. to about 100° C.

13. The method of claim 1, wherein the composition comprises sugar acetate, sugar ether, sugar ketals, or sugar acetonides.

14. The method of claim 1, wherein the reactor is a batch reactor.

15. The method of claim 1, wherein the reaction is greater than 50% selective to forming a combination of HMF-acetate, or HMF-ether, HMF, and LA and/or LA ester versus tar and char.

16. The method of claim 1, wherein the sugar and sugar acetate, sugar ether, or sugar acetonide conversion does not exceed 75% conversion during the reaction.

17. The method of claim 1, further comprising reacting the HMF-derivative into a second product.

18. The method of claim 1, further comprising the steps of extracting the carboxylic acid, alcohol or ketone from any water and sugar after the reaction before it is recycled back into the reactor.

19. The method of claim 1, further comprising the step of removing any soluble tars from the sugar, sugar acetates, sugar ethers, sugar acetonides, or sugar ketals by precipitation into water or another co-solvent.

20. The method of claim 1, further comprising the step of removing any soluble tars from the sugar, sugar acetates, sugar ethers, sugar acetonides, or sugar ketals by extraction into an extraction solvent.

* * * * *

UNITED STATES PATENT AND TRADEMARK OFFICE
CERTIFICATE OF CORRECTION

PATENT NO. : 10,316,009 B2  
APPLICATION NO. : 15/754060  
DATED : June 11, 2019  
INVENTOR(S) : Brian D. Mullen et al.

Page 1 of 1

It is certified that error appears in the above-identified patent and that said Letters Patent is hereby corrected as shown below:

In the Claims

In Claim 6, on Column 34, Line 38, replace "contain" with --contains--.

Signed and Sealed this  
Fourteenth Day of July, 2020

Andrei Iancu  
*Director of the United States Patent and Trademark Office*